(12) United States Patent
Eberli et al.

(10) Patent No.: US 8,951,241 B2
(45) Date of Patent: Feb. 10, 2015

(54) PREVENTION OF BACTERIAL ADHERENCE AND GROWTH IN AN UROLOGICAL IMPLANT

(75) Inventors: Daniel Eberli, Zurich (CH); Lukas Hefermehl, Zurich (CH); Michael Gabi, Zurich (CH); Alexandre Lar-Magnac, Zurich (CH); Janos Voros, Zurich (CH)

(73) Assignees: Universitat Zurich, Zurich (CH); ETH Zurich, Zurich (CH)

( * ) Notice: Subject to any disclaimer, the term of this patent is extended or adjusted under 35 U.S.C. 154(b) by 23 days.

(21) Appl. No.: 13/810,221

(22) PCT Filed: Jul. 6, 2011

(86) PCT No.: PCT/EP2011/061389
§ 371 (c)(1),
(2), (4) Date: Jan. 15, 2013

(87) PCT Pub. No.: WO2012/007330
PCT Pub. Date: Jan. 19, 2012

(65) Prior Publication Data
US 2013/0123756 A1     May 16, 2013

(30) Foreign Application Priority Data
Jul. 16, 2010   (CH) ...................................... 1163/10

(51) Int. Cl.
| | | |
|---|---|---|
| *A61M 25/01* | (2006.01) | |
| *A61F 2/04* | (2013.01) | |
| *A61F 2/82* | (2013.01) | |
| *A61M 25/00* | (2006.01) | |
| *A61M 27/00* | (2006.01) | |
| *A61N 1/20* | (2006.01) | |
| *A61N 1/36* | (2006.01) | |
| *A61N 1/378* | (2006.01) | |

(52) U.S. Cl.
CPC ... *A61F 2/04* (2013.01); *A61F 2/82* (2013.01); *A61M 25/0017* (2013.01); *A61M 27/008* (2013.01); *A61N 1/20* (2013.01); *A61N 1/36007* (2013.01); *A61N 1/3787* (2013.01); *A61F 2002/047* (2013.01); *A61F 2002/048* (2013.01); *A61F 2250/0001* (2013.01)
USPC ........... 604/544; 604/508; 604/264; 604/265; 607/116

(58) Field of Classification Search
CPC .......... A61M 25/0017; A61M 25/002; A61M 2025/0056; A61F 2/04
USPC ............. 623/23.65–23.68; 607/116; 604/264, 604/508, 544, 265
See application file for complete search history.

(56) References Cited

U.S. PATENT DOCUMENTS

| | | | | |
|---|---|---|---|---|
| 4,411,648 | A | * | 10/1983 | Davis et al. ...................... 604/21 |
| 4,569,673 | A | | 2/1986 | Tesi |
| 5,078,736 | A | * | 1/1992 | Behl ............................ 623/1.15 |
| 5,260,020 | A | | 11/1993 | Wilk et al. |
| 2007/0032861 | A1 | | 2/2007 | Weber et al. |
| 2007/0191816 | A1 | * | 8/2007 | Behan et al. ............... 604/890.1 |
| 2010/0233021 | A1 | | 9/2010 | Sliwa et al. |

* cited by examiner

*Primary Examiner* — Christopher D Koharski
*Assistant Examiner* — Michael Carey
(74) *Attorney, Agent, or Firm* — JMB Davis Ben-David

(57) ABSTRACT

A medical device is disclosed, which comprises a functional unit (C) for permanent or temporary placement in the urogenital tract of a human or animal body. The functional unit has at least one electrically conducting portion. A power source (G) supplies a current to the electrically conducting portion after placement of the functional unit in the urogenital tract. In this manner, the growth of bacteria on the functional unit can be reduced.

19 Claims, 8 Drawing Sheets

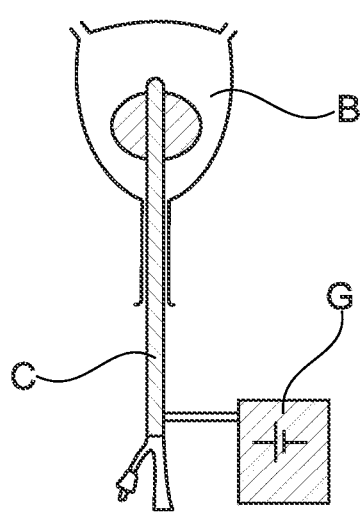
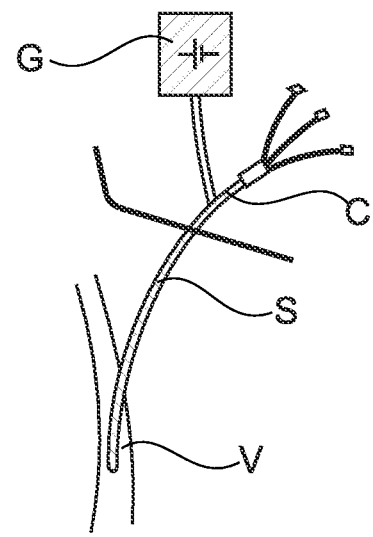
Fig. 1          Fig. 2
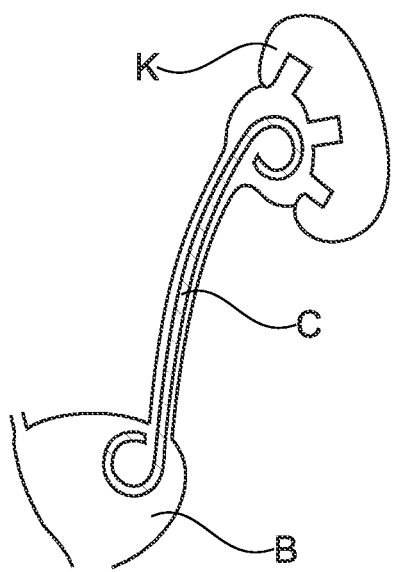
Fig. 3

PREVENTION OF BACTERIAL ADHERENCE AND GROWTH IN AN UROLOGICAL IMPLANT

CROSS-REFERENCE TO RELATED APPLICATIONS

This is the U.S. National Stage of International Application No. PCT/EP2011/061389, filed Jul. 6, 2011, which was published in English under PCT Article 21(2), which in turn claims the benifit of Switzerland Patent Application No. 01163/10, filed Jul. 16, 2010.

TECHNICAL FIELD

The present invention relates to a medical device comprising a functional unit for temporary or permanent placement in the urogenital tract of a human or animal body, where it is in contact with urine, and to a method of reducing bacterial growth and/or encrustation on such a device after placement in the urogenital tract.

PRIOR ART

Urogenital catheters, including Foley catheters and urethral stents, are commonly used in patients with obstructive disease to secure urine flow. If used only short term the newer generation catheters offer good comfort with minimal complications. However, in situations where long-term catheters are needed, the rate of bacterial colonization, infection and encrustation remains a significant clinical problem. The foreign body serves as a bacterial reservoir, which can then trigger severe urinary infections requiring the administration of antibiotics and replacement of the catheter. Approximately, half of all patients with long term indwelling catheters will suffer complications for encrustation and blockage by bacterial films over time. A prospective observation of 467 patients with Foley catheters in community care revealed 506 emergency referrals in 6 months, mainly due to catheter blockage. These procedures are a burden to the health care cost and significantly affect the quality of life of patients.

Despite the knowledge of adherence and growth of bacteria, no stent material and no surface coating completely resists the adherence of bacteria. Upon insertion of a prosthetic device in the urine tract, a conditioning film is formed on the device surface. The film, being composed of proteins, electrolytes, and other organic molecules, changes the device's surface properties and may provide receptor sites for bacterial adhesion. Once the bacteria can adhere to the biofilm, cell division and colonization starts and may lead to large coherent bacterial biofilms and encrustation. This can then lead to superinfection by opportunistic bacteria and to a rapid expanding infection often resistant to common antibiotics, especially if preceding antibiotic treatment has failed. Biofilms offer an optimal environment for bacterial growth since there is no immunologic response and the penetration of antibiotics is poor.

Many approaches to prevent biofilm formation and consecutive encrustation of urogenital catheters have been proposed with various outcomes [Williams, G. J. and D. J. Stickler, Some Observations on the Diffusion of Antimicrobial Agents Through the Retention Balloons of Foley Catheters. The Journal of Urology, 2007, 178(2): p. 697-701; Schierholz, J. M., et al., Antiinfective and encrustation-inhibiting materials—myth and facts. International Journal of Antimicrobial Agents, 2002, 19(6): p. 511-516; Stickler, D. J. and S. D. Morgan, Observations on the development of the crystalline bacterial biofilms that encrust and block Foley catheters. Journal of Hospital Infection, 2008. 69(4): p. 350-360.]. Hydrophilic outer layers or coating with antibacterial agents such as rifampicinlminocycline or silver-ions, have been used to make urethral catheters less attractive to bacterial colonization [Davis, C. P., et al., Effects of microamperage, medium, and bacterial concentration on iontophoretic killing of bacteria in fluid. Antimicrob. Agents Chemother., 1989, 33(4): p. 442-447.]. While drug eluting catheters were able to reduce bacterial growth the formation of Calcium-Phosphate encrustation could not be inhibited. Further, the use of long term antibiotic agents is associated with the development of resistant microorganisms.

Besides material research, other approaches tested were electric current to increase the efficacy of antibiotics against bacterial biofilms using high-frequency electric fields [Giladi, M., et al., Microbial growth inhibition by alternating electric fields. Antimicrobial Agents and Chemotherapy, 2008. 52(10): p. 3517-3522]. In 1969 Pareilleux and coworkers have first demonstrated the bactericidal effect of electric current [Pareilleux, A. and N. Sicard, Lethal Effects of Electric Current on *Escherichia coli*. Appl. Environ. Microbiol., 1970, 19(3): p. 421-424.]. An electrified drain to sterilize the field of postoperative wound drainage was reported in 1993 [Shafik, A., The electrified catheter. World Journal of Urology, 1993, 11(3): p. 183-185; Shafik, A., The electrified drain. A new device for sterilizing the field of drainage. International surgery, 1993, 78(4): p. 357-9.]. A newer catheter device that would resist encrustation by *Proteus mirabilis* biofilms required relatively high current that could only be provided at the tip of the catheter, where fast corroding silver electrodes were located [Chakravarti, A., et al., An electrified catheter to resist encrustation by *Proteus mirabilis* biofilm. Journal of Urology, 2005, 174(3): p. 1129-1132.]. This catheter increased the amount of silver ions in the urine and was able to decrease the rate of encrustation significantly.

In [M. Gabi et al., "Electrically controlling cell adhesion, growth and migration", Colloids and Surfaces B: Biointerfaces 79 (2010) 365-371], the adhesion, growth and migration of C2Cl2 myoblasts on a specifically designed neurochip with indium-tin oxide (ITO) microelectrodes has been investigated, and it has been found that small current densities in the range of approximately 500 $nA/mm^2$ can effectively inhibit the migration of myoblasts in the specific setup investigated if supplied with a sufficiently high current dose. In [M. Gabi et al., "Influence of applied currents on the viability of cells close to microelectrodes"], it was shown that myoblasts directly cultured on microelectrodes undergo cell death when exposed to current densities above 570 $nA/mm^2$. These results, obtained in vitro on myoblasts, cannot be readily transferred to the growth of bacteria in the presence of urine, and consequently applications to the urogenital tract are described or suggested in these documents.

SUMMARY OF THE INVENTION

It is an object of the present invention to reduce bacterial growth and biofilm formation on a functional unit inserted into the urogenital tract of a living human or animal body.

This object is achieved by a device as laid down in claim 1.

In a second aspect, it is an object of the present invention to provide a method of reducing the growth of bacteria on a functional unit inserted into the urogenital tract of a living human or animal body.

This object is achieved by a method as laid down in claim 18.

Further embodiments of the invention are laid down in the dependent claims.

Accordingly, a medical device is suggested, comprising:
    a functional unit for permanent or temporary placement in the urogenital tract (including kidney, renal pelvis, ureter, urinary bladder and urethra) of a living human or animal body (in the following also called the "patient body"), the functional unit having at least one electrically conducting portion; and a power source operable to supply a voltage and/or current to the electrically conducting portion after placement of the functional unit in the urogenital tract in a manner effective to reduce the growth of bacteria and/or encrustation on the functional unit.

The inventors have shown that bacterial growth and adhesion on functional units that are in contact with urine as well as encrustation can be effectively reduced by the application of suitable currents or voltages. The voltage and/or current may be supplied locally to the active unit only, e.g. for releasing drugs from the functional unit or for heating the active unit, as described in more detail below. However, it is preferred that the current causes a small current flow between the functional unit and surrounding material of the patient body, e.g., for electrochemically changing the environment of the active unit.

In particular, it is preferred that the power source is operable to apply the current in a manner to generate a surface current density between 10 nA/mm$^2$ (nanoamperes per square millimeter; 1 nA/mm$^2$=0.001 A/m$^2$) and 10,000 nA/mm$^2$ between a surface of said functional unit and environmental body material. The term "environmental body material" is to be understood broadly as encompassing any material of the patient body in the vicinity of the inserted functional unit. The material may be in direct contact with the functional unit or may be separated from the functional unit by other body material. Body materials include but are not limited to muscle tissue, mucosa, fat tissue, blood, urine and other body fluids etc.

In particular, surface current densities between 50 nA/mm$^2$ and 2,000 nA/mm$^2$ are preferred. More preferably, the surface current density is between 200 nA/mm$^2$ and 1,000 nA/mm$^2$. If the current density is too low, its effect might not be sufficient to reduce bacterial growth and biofilm formation to the desired degree. On the other hand, if the current density is too high, increased electrophoretic and electrolytic/electrochemical effects might lead to undesired side effects.

The power source is preferably operable to actively control the voltage and/or current that is supplied to the functional unit so as to ensure that the current density stays in the desired range. Power sources providing a well-defined current with a predetermined magnitude are well known in the field of electronics and are then usually called current sources. However, in simple embodiments, it may be sufficient to supply the current without actively controlling its magnitude, e.g., by simply maintaining a predetermined voltage between two electrodes of which at least one is connected to the functional unit. The power source may be wholly or partially integrated with the functional unit (i.e., the functional unit and at least parts of the power source may together form a single unit to be placed wholly or partially inside the patient body), or it may be disposed remote from the functional unit, being connected to the functional unit by wires or supplying energy to the functional unit in other ways, as further detailed below.

In preferred embodiments, the voltage and/or current is supplied as an alternating voltage or alternating current. In particular, if surface currents in surrounding body material are to be excited, it is preferred to supply the current as a low-frequency alternating current, in particular, below 1 kHz or even below 10 Hz. Good results have been achieved with currents having a frequency in the range between 0.1 Hz and 1 Hz (i.e. with periods in the range of 1 second to 10 seconds).

In other embodiments, the current may be applied as a direct current with a single polarity only. In this case, it is preferred if the functional unit acts as the anode for the current, with a counter electrode acting as the cathode, to prevent deposition of inorganic materials such as calcium and magnesium phosphates. However, it is also possible that the functional unit acts as the cathode, or that different portions of the functional unit act as the cathode and anode, respectively.

For supplying the power source with energy, the power source may comprise a battery. The battery may be disposed in a separate housing or, preferably, in a common housing with the rest of the power source. In some embodiments, the power source, including the battery, and the functional unit may form a single, self-supported unit to be placed wholly inside the patient body. This is preferred for functional units such as uretric stents or prostatic stents, which are normally placed wholly inside the patient body without any connection to the outside. The battery may be disposable or rechargeable. If the battery is rechargeable, the power source may comprise means for supplying recharging energy to the battery, as detailed below.

In some embodiments, energy may be supplied to the functional unit in a contact-less manner, transcutaneously from outside the patient body, either permanently during operation of the device, as in the case where no additional energy source or energy storage means associated with the functional unit are available, or intermittently, as in the case when a rechargeable battery or other rechargeable energy storage means such as a large capacitance is associated with the functional unit inside the patient body. In such embodiments, the power source will generally comprise an energy transmitter to be placed outside the human or animal body, the energy transmitter being operable to transmit energy from outside the body to a location inside the body in a contact-less fashion, and an implantable energy receiver operable to receive energy from the energy transmitter in a contact-less fashion when implanted in the body. Various means for transmitting energy from outside a body to inside a body in a contact-less fashion are known, e.g., from the technical field of cardiac pacemakers or implantable medicament pumps. The most widely employed principle in such applications is inductive, i.e., an inductive coupling between the energy transmitter and the energy receiver is established, much like in a (core-less) transformer. For an example, see WO 2010/042054 and references therein. In more general terms, the energy transmitter is in such cases operable to generate an (alternating) electromagnetic field, and the energy receiver is operable to receive the electromagnetic field generated by the energy transmitter and to convert said electromagnetic field into an electrical current, as known in the art. Alternative means for energy transmission might include the transmission of light, of X-rays, of heat or of mechanical vibrations, including ultrasound vibrations.

In other embodiments, the battery or any other energy source is placed outside the patient body and connected directly or indirectly to the functional unit by wires. This can be accomplished easily for such functional units such a Foley catheters or nephrostomy catheters, which establish a connection between the inside and the outside of the body already by themselves.

As the functional unit is generally inserted in the inside of the urogenital tract, in particular, in an urogenital tube like the ureter and/or urethra, an additional problem arises of how to supply energy from the outside of the tube to its inside, through the wall of the tube. In the simplest case, wires extending through the tube wall or to the tube end may be used. However, it would be desirable to transmit energy from a location outside the ureter or urethra to the functional unit inside the ureter or urethra in a contact-less fashion.

In first preferred embodiments, this is achieved by inductive coupling. The functional unit may be inductively coupled to an inductor outside of the urogenital tube (ureter or urethra), e.g. to a solenoid coil placed around the tube or even outside of the patient body, to generate a magnetic field at the location of the functional unit that induces a voltage in an inductor associated with the functional unit. In other words, the power source then comprises a first inductor that can be placed outside of an urogenital tube (inside or outside of the patient body) and operable to generate a substantial magnetic field acting on the functional unit, and a voltage generator operable to supply said first inductor with a time-dependent first voltage. The functional unit then comprises a second inductor (which may be represented by the functional unit itself) which, after placement of the functional unit inside the tube and of the first inductor outside of the tube, is inductively coupled with said first inductor through the tube wall. In this manner, a second voltage may be induced in the second inductor via a time-dependent magnetic field generated by a time-dependent current in the first inductor caused by the first voltage.

The (generally time-dependent) voltage induced in the second inductor may cause a current in the functional unit and possibly in the surrounding body material in a variety of different ways.

In some embodiments, the functional unit has a first and a second electrode connected to the second inductor, and, after placement of the functional unit in the urogenital tract, the first and second electrodes are electrically connected with environmental body material in a manner that the second voltage causes a current to flow through the body material. In this case the first and second electrodes act as anode and cathode, respectively, i.e., no separate, remote counter electrode is required. Instead of a direct coupling of the second inductor to electrodes, the voltage may first be rectified by a suitable rectifier (a diode in the simplest case), and the rectified voltage may be supplied to the electrodes. A control circuit for controlling the magnitude of the resulting current may further be associated with the functional unit.

The present invention also provides a functional unit which is particularly adapted for this kind of operation. Such an implantable functional unit for placement in the urogenital tract will have at least two electrodes connectable to environmental body material, the electrodes acting as the terminals of an inductor operable to receive a time-dependent magnetic field so as to induce a voltage between said electrodes. The functional unit may, in particular, be a stent, defining a stent axis by its long (tube) axis. The inductor then preferably defines a substantially helicoidal current path around said stent axis.

In alternative embodiments, the second inductor may have a first and a second terminal which are connected directly or indirectly, without the involvement of any environmental body material, to form a closed circuit with the second inductor. In particular, the terminals may be electrically connected by a connection having a low ohmic resistance (e.g., the terminals may essentially be shorted). The terminals may be electrically insulated from the environmental body material. The voltage generator may then be operable to supply the time-dependent first voltage in a manner to induce a closed-loop current in the closed circuit. This is particularly useful if the functional unit comprises a drug releasable from the functional unit by the application of such a current, e.g., by having a drug-eluting coating whose elution rate may be controlled by current. The drug may be released electrophoretically or by electrochemical means, or by a (possibly local) heating of a portion of the stent due to the current.

In second preferred embodiments, energy is supplied to the functional unit through the tube wall by a capacitive coupling. In this case, the power source may comprise:
  a first electrode placed in the vicinity of said functional unit to form a first capacitance with the functional unit;
  a second electrode placed in environmental body tissue to form a second capacitance with the functional unit; and
  a voltage generator operable to supply said first electrode and said second electrode with a time-dependent first voltage so as to cause a capacitive current between the first electrode and the functional unit and an ionic current between the functional unit and the second electrode.

The first electrode is preferably electrically insulated from the functional unit and from the surrounding body material. It may partially or fully surround the functional unit. The second electrode may be placed remote from the first electrode and from the functional unit, in electrical connection with the surrounding body material. Likewise, the functional unit is required in this case to have an electrical connection with the surrounding body material.

In further alternative embodiments, the power source may comprise an implantable electrical generator operable to transform mechanical energy into electrical energy. The electrical generator may then be operable to transform mechanical energy associated with blood or urine flow, with tissue moving, with deformations of the functional unit in the urether or urethra by body or organ movements, or with general other body movements into electrical energy.

As already mentioned, the functional unit may contain a drug, the release of the drug being controllable by a voltage and/or current applied to the unit. In particular, it is conceivable that direct electrolytic/electrochemical or electrophoretic effects might lead to a release of a drug associated with the stent. In particular, the functional unit may comprise a drug-releasing coating, and the device may then be operable to control release of a drug from the coating by means of said voltage and/or current. Materials that are well suited for electrically controlled drug release are disclosed in the following documents:

P. Bawa et al., Stimuli-responsive polymers and their applications in drug delivery, Biomedical Materials 4 (2009), 022001, pp. 1-15;
  X. Luo et al., Sponge-like nanostructured conducting polymers for electrically controlled drug release, Electrochemistry Communications 11 (2009), 1956-1959;
  S. Kim, Engineered polymers for advanced drug delivery, European Journal of Pharmaceutics and Biopharmaceutics 71 (2009), 420-430;
  I. Tokarev et al., Stimuli-responsive hydrogel thin films, Soft Matter 5 (2009), 511-524;
  Y. Qiu et al., Environment-sensitive hydrogels for drug delivery, Advanced Drug Delivery Reviews 53 (2001), 321-339;
  F. Boulmedais et al., Controlled Electrodissolution of Polyelectrolyte Multilayers: A Platform Technology Towards the Surface-Initiated Delivery of Drugs, Advanced Functional Materials, 16 (1): 63-70, 2006.

It is also conceivable to control the release of the drug by (local) heating of stent material.

The functional unit may be fully or at least partially resorbable, and the device may then be operable to control a rate of resorption by means of the voltage or current.

The electrically conductive portions of the functional unit are preferably electrochemically inert under the conditions employed. They may be made of any of the following:

a metal or a semiconductor, in particular, Au, Ag, Ir, Ni, Cr, Co, Pt, C, Cu, Al, Ti, In, Sn, Si and any combination of thereof, in bulk form or in the form of a porous matrix;

an electrically conductive polymer, in particular, poly(acetylene)s, poly(pyrrole), poly(thiophene), polyanilines, polythiophene, poly(p-phenylene sulfide), poly(p-phenylene vinylene)s, polyindole, polypyrene, polycarbazole, polyazulene, polyazepine, poly(fluorene), or polynaphthalene;

a combination of metallic particles and at least one conductive polymer; or a polymer matrix (in particular, silicone, polyurethane or other known polymeric implant materials) with an electrically conductive filler material in the form of particles, fibers, or nanotubes, wherein the filler material may e.g. be made of Au, Ag, Ir, Ni, Cr, Co, Pt, C, Cu, Fe, Al, Ti, In, Sn, Si and any combination of thereof.

The associated method aims at reducing bacterial growth and encrustation on a functional unit inserted into the urogenital tract of a human or animal body, where the functional unit is in contact with urine. The method comprises applying a voltage and/or current to the functional unit after insertion into the urogenital tract in a manner effective to reduce bacterial growth and encrustation.

The same consideration apply for this method as for the device discussed hereinabove, in particular, the considerations concerning current density, application in as alternating or direct current, and transmission of energy to the active unit.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein FIG. 1 shows a device with a Foley catheter placed into the urinary bladder as a functional unit;

FIG. 2 shows a device with an intravenous line as a functional unit;

FIG. 3 shows a device with a double-J stent placed between kidney and bladder as a functional unit;

DESCRIPTION OF PREFERRED EMBODIMENTS

FIG. 1 shows a medical device according to a first embodiment of the present invention. The device comprises a functional unit C in the form of a Foley catheter inserted into the urinary bladder B through the urethra. The catheter has a conductive surface. To this end, the catheter is made from silicone and coated with a thin layer of platinum or another conducting material as detailed above. A small current with a surface current density in the range of a few tens to a few hundred nA/mm$^2$ is generated between the catheter and the surrounding body material. This current is supplied and actively controlled at a set current level by a battery-powered power source G placed outside of the patient body, which is connected to the catheter by a flexible electric wire. Power sources capable of providing a well-defined, controlled current are well known in the art and are commercially available.

A current may also be applied to catheters in other fields than urology. FIG. 2 shows a medical device where the functional unit is an intravenous line. A jugular catheter C made of latex protrudes through the skin S and into a vein V. The catheter is coated with a conductive polymer. Current is supplied to the catheter by a power source G which is again placed outside of the patient body and is connected to the catheter by a flexible electrical wire. In the same manner, a nephrostomy catheter may be coated with an electrically conducting coating and may be provided with a current so as to generate a surface current density between the catheter and surrounding body tissue in the range of a few tens to a few hundred nA/mm$^2$.

FIG. 3 shows a medical device according to a further embodiment of the present invention. Here the functional unit is a double-J ureteral stent. The functional unit C which is suitable to be placed between the urinary bladder B and the kidney K is covered with a conductive surface. A power supply (not shown) is placed outside the body cavity and transmits electrical power via induction to the functional unit.

Figure 4:
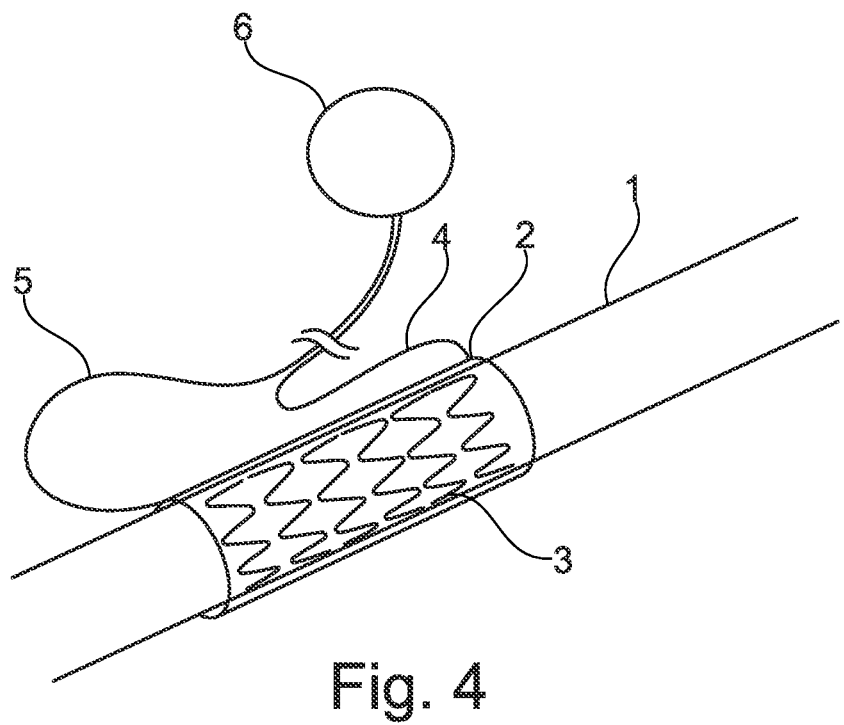
FIG. 4 shows a stent implanted in an urogenital tube, to which current is supplied inductively.

FIG. 4 illustrates a further embodiment of the present invention. A stent 3 is placed in an urogenital tube 1, e.g., in the ureter or in the urethra. An inductor 2, e.g., in the form of a solenoid coil wound around the tube, is placed in the vicinity of the stent 3 outside the tube 1. An AC voltage or, more generally, a time-dependent voltage is supplied to the inductor 2 from an implanted or extracorporeal voltage generator 6 through wires 4 and 5. The time-dependent voltage causes a time-dependent current to flow through the inductor 2. This current causes a time-varying magnetic field B that permeates the stent, as illustrated in FIG. 2. The time-varying magnetic field causes a time-dependent voltage to be induced in the conducting portions of the stent.

Figure 5:
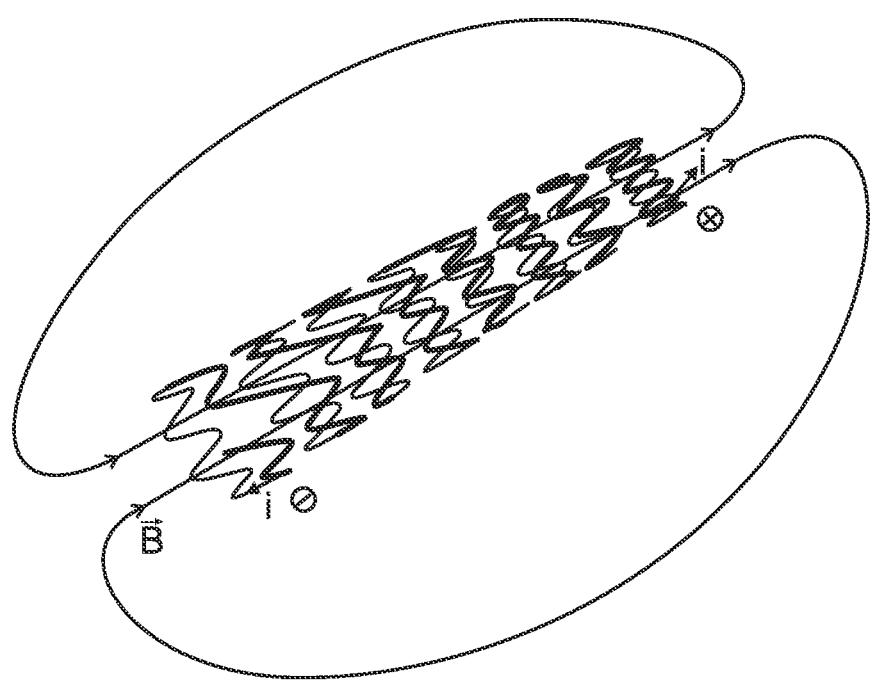
FIG. 5 shows a stent in which a current is driven inductively.

In particular, the stent may act as an inductor comprising a single, meandering but generally helical conducting path, as illustrated in FIG. 5. The stent will thus act as a second solenoid coil. In this case, the induced time-dependent voltage will be available at the terminals of this conducting path. In contrast, in commercially available stents no such open-loop conducting path will generally exist.

This voltage may be used in a variety of ways to generate currents. In one embodiment, the conducting path is short-circuited. Current flow is then restricted to the stent in a closed current loop, and no current will flow in the environmental body material. This current flow may be used to release a drug in a controlled manner if the stent comprises a drug-eluting coating or if drugs are otherwise embedded in the stent. This can be done by the current causing electrochemical reactions in the stent for releasing the drug. The induced current will also cause some ohmic heating of the conducting path. If strong enough, this local heating may likewise be employed to release a drug from the stent.

In other embodiments, the induced voltage may be used to cause a current i through the tissue and urine in the immediate surroundings of the stent. The current may be rectified by a diode or a bridge rectifier, if desired, and its magnitude may be electronically controlled by a control circuit (not shown).

Figure 6:
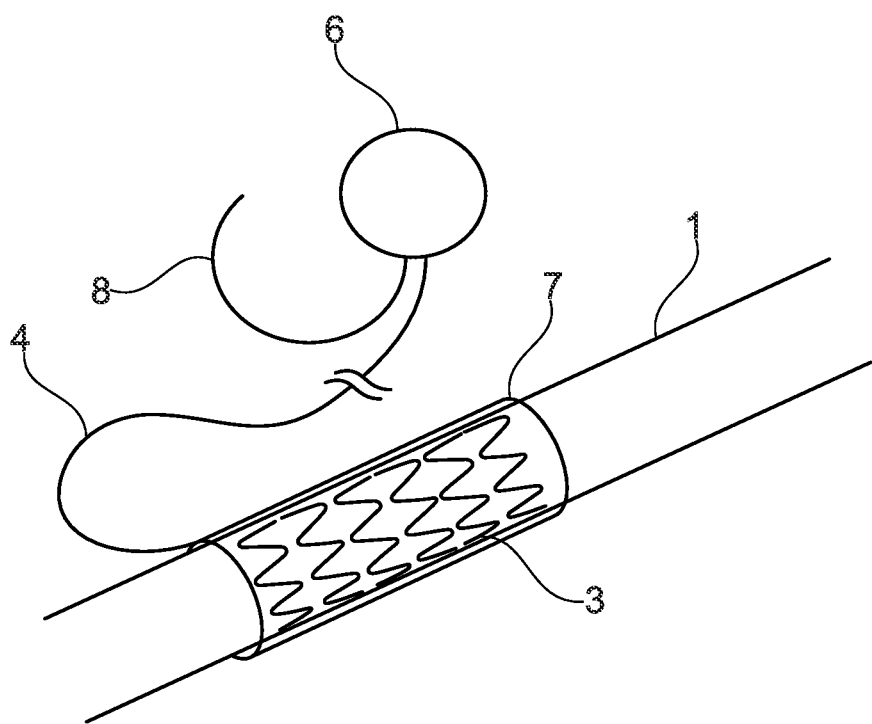
FIG. 6 shows a stent implanted in an urogenital tube, to which a capacitive current is supplied.

FIG. 6 illustrates yet another embodiment. Here the stent 3 is surrounded by a cylindrical electrode 7. This electrode is electrically insulated from the stent and from the surrounding body tissue. A counter electrode 8 is placed in some surrounding body tissue to be in electrical contact with this tissue. An AC voltage or, more generally, a time-dependent voltage is applied by generator 6 to the electrode 7 and to the counter electrode 8. This causes a capacitive current to flow between the electrode 7 and the stent 3, and an ionic current to flow between the stent 3 and the counter electrode 8. In other words, an ionic pathway is formed between the stent 3 and the counter electrode 8. The current generated by the generator 6 will be transmitted capacitively from the electrode 7 to the stent 3 and electrochemically from the stent 3 to the counter electrode 8 through the environmental body material. In reality, also non-negligible ohmic losses and stray inductances might contribute to the equivalent circuit diagram. This arrangement is particularly suited to cause currents between the stent and environmental body material such as urine and tissue.

In the embodiments of FIGS. 4-6, the stent may be replaced by any other functional unit to be inserted into a urogenital tube.

Figure 7:
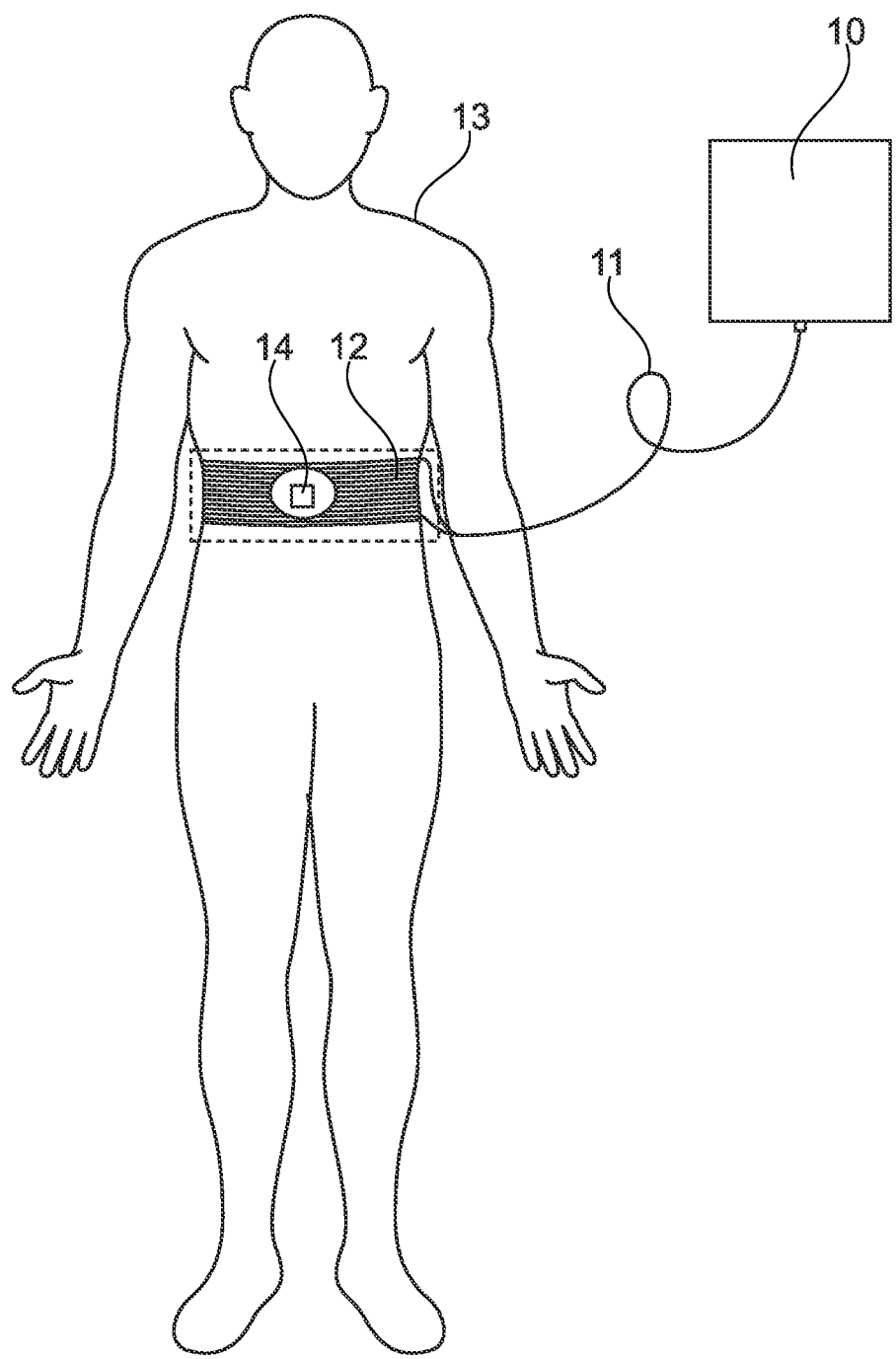
FIG. 7 is a sketch illustrated how the functional unit can be supplied with energy transcutaneously in a contact-less manner.
Figure 8:
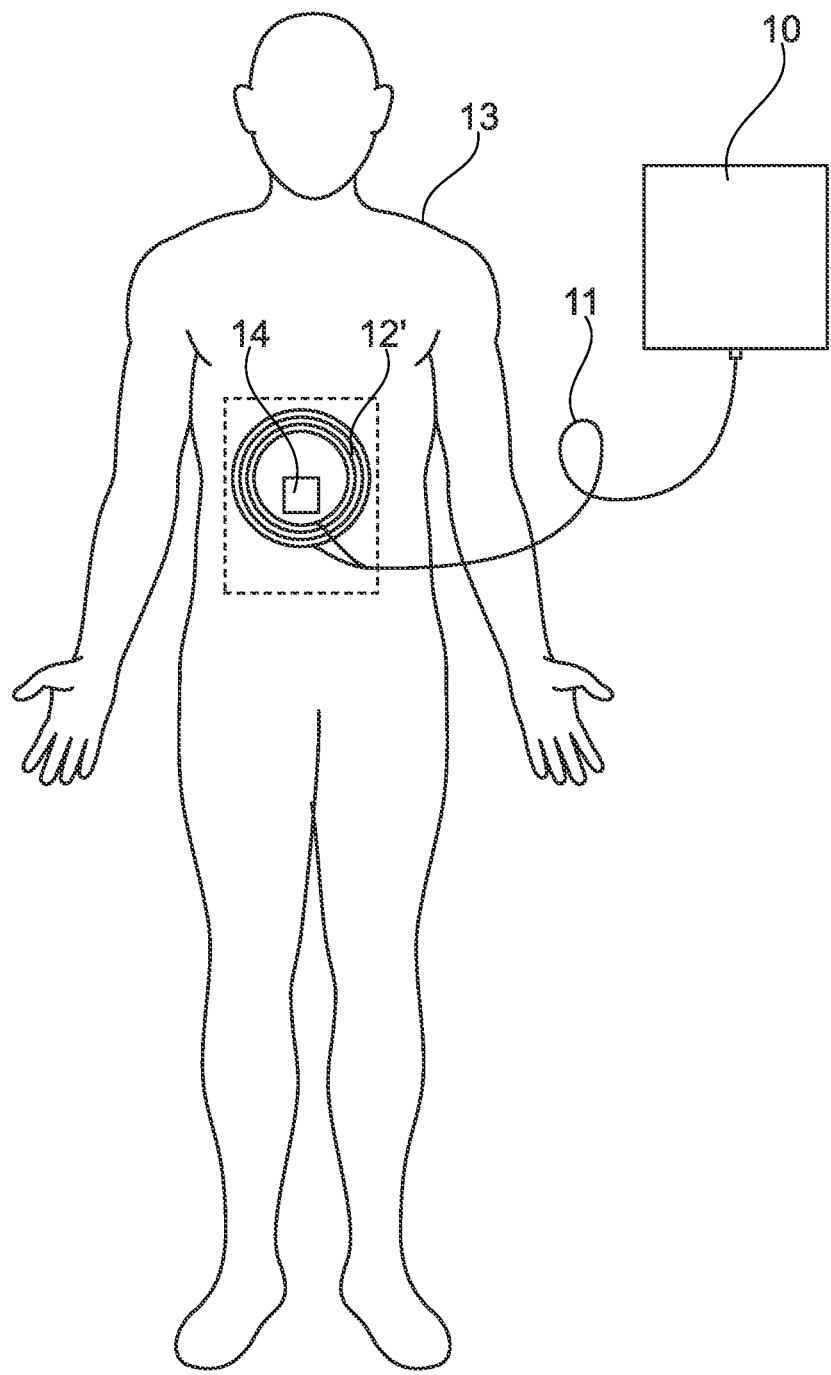
FIG. 8 is a sketch illustrating an alternative embodiment of supplying the functional unit with energy in a contact-less manner.

FIGS. 7 and 8 illustrate two possibilities of how the functional unit may be supplied with energy in a contact-less fashion. A patient 13 has been implanted with a urogenital functional unit (not shown). An internal power supply 14 is implanted in the body. The power supply acts as a power source for the functional unit, either directly through surgical wires, or indirectly, e.g. through inductive or capacitive means as described above in conjunction with FIGS. 4-6. A primary coil 12 is wound around the body of the patient. The primary coil 12 is connected to an external power supply 10 by a cable 11. The external power supply supplies a time-dependent electric current to coil 12, which causes a time-dependent magnetic field acting at the location of the internal power supply. By the time-dependent magnetic field, a secondary voltage is induced in a pickup coil (not shown) of the internal power supply. This secondary voltage is used either to directly power the stent, or to recharge a storage capacitor or battery in the secondary power supply. Alternatively, the internal power supply may also be omitted entirely, and the time-dependent magnetic field may act to directly induce a secondary voltage in the functional unit itself, as described above in conjunction with FIGS. 4 and 5.

An alternative embodiment is shown in FIG. 8. Like parts are denoted with the same reference signs as in FIG. 7. Instead of a primary coil wound around the body, the primary coil 12' in this embodiment is a flat coil placed on the skin of the patient. While the direction of the magnetic field generated by this primary coil is different than in the embodiment of FIG. 7, the principle of operation is the same.

EXAMPLE

Feasibility Study in vitro

The reduction of the buildup of naturally forming conditioning films was proven by applying different current densities to a platinum electrode chip in a flow chamber subjected to urine flow. The film formation and desorption in artificial urine was analyzed by highly mass sensitive quartz crystal microbalance (QCM) and surface sensitive atomic force microscopy. The dissolution behavior was later tested by dipping the formed films on the QCM crystal in acidic or base solution. Finally, bacterial adherence, growth and survival were assessed using a defined environment with *Proteus mirabilis* in artificial urine.

A. Experimental a. Platinum Electrode Chip and Flow Cell Fabrication Procedure

Figure 9:
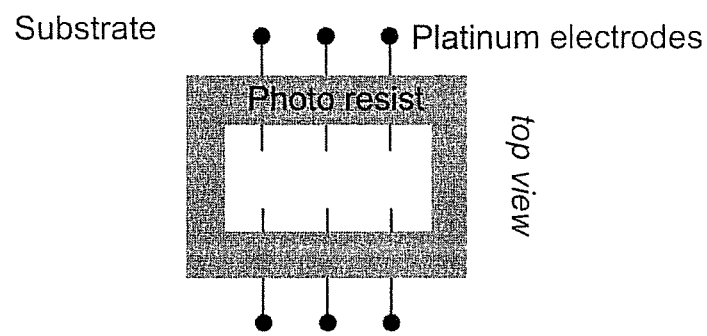
FIG. 9 shows a schematic representation of a glass substrate with six equal platinum electrodes on a microscopy cover slide insulated by a photo resist layer, for use in a custom built flow cell to test bacterial adhesion and film formation.

The chip was designed to contain six equal electrode surfaces inside the flow chamber (FIG. 9). The substrate was fabricated using a glass microscopy cover slide, that was cleaned for 5 minutes with Piranha solution, a mixture of $H_2SO_4$ and $H_2O_2$, used remove organic residues from substrates, then rinsed with $H_2O$ and blow dried with $N_2$. The slide was heated on a hot plate at 200° C. for 20 min, immediately cooled down to room temperature and then spin coated with ma-N400 photoresist (micro resist, Germany) at 3000 rpm for 30 sec. The slide was then pre-baked on a hot plate at 100° C. for 2 min before exposing for 2 min in a Karl Süss X380 mask aligner through a polymer mask. The photoresist was developed in ma-D533/S solution (micro resist, Germany) for 30 sec and rinsed in H2O. The slide was etched in oxygen plasma for 3 min to remove any polymer residues after the rinsing step and to increase the adhesion of the following metal layer. A thin film of titanium (30 nm) and platinum (40 nm) were deposited subsequently on the slide by physical vapor deposition (PVD) (Pfeiffer Classic 500, Wetzler, Germany). After deposition, the photoresist lift-off was performed in N-Methyl-2-pyrrolidone (NMP) and the slide was cleaned with acetone, isopropanol and blow dried with N2. A layer of S1818 photoresist (Shipley, USA) was spin coated over the electrodes to insulate the electrode leads and present only 0.2×1 mm platinum surface to the artificial urine.

Figure 10:
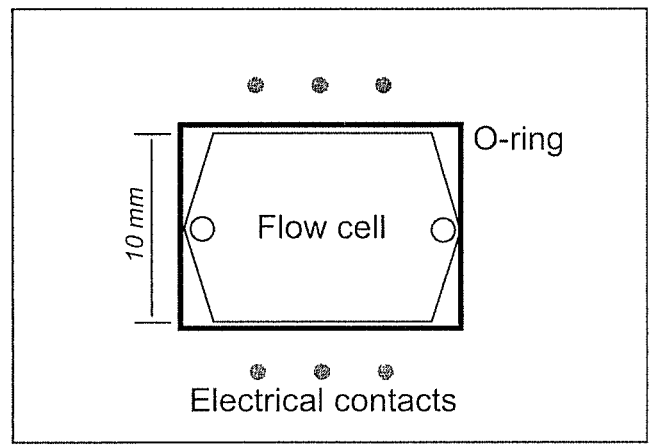
FIG. 10 shows a top view of the flow cell with electrical spring contacts and silicone O-ring to prevent any leakage.
Figure 11:
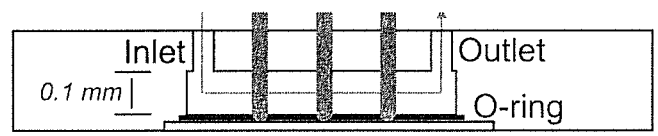
FIG. 11 shows a side view of the flow cell with mounted substrate and urine flow direction indicated by the arrow.

The flow chamber was custom-built, made of PMMA and designed for hosting the chip substrate (FIGS. 10 and 11). Gold spring contacts enabled a simple access from outside the flow cell to the platinum electrodes. The flow chamber itself is liquid tightly sealed by an O-ring and has the dimensions width=10 mm (W), length=15 mm and height=0.1 mm (H). A peristaltic pump (IPC, ISMATEC, Switzerland) was used to maintain a constant flow rate of Q=200 gl/min. The flow chamber was placed in an incubator at 37° C. during the experiment, while the urine reservoir was placed outside of the incubator at room temperature. Selected currents were applied by the Autolab potentiostat (Eco Chemie, Netherlands).

b. Artificial Urine and Bacteria

A concentrated (5×) stock solution was prepared and accordingly diluted in $H_2O$ before starting the QCM-D experiment (see below). Before the flow cell experiment, an aliquot of *Proteus mirabilis* was diluted in 500 ml sterile artificial urine. The aliquot was made by scratching the bacteria from the culture media and suspending in 10 ml phosphate buffered saline (PBS) pH 7.4 and store in portions of 0.5 ml at −20° C. The density of bacteria was determined by measuring the Absorbance OD at 600 nm (McFarland Standard). The final concentration of bacteria used in the experiments was of $2 \times 10^6$ CFU/ml.

c. Electrochemical Quartz Crystal Microbalance with Dissipation Monitoring (EC-QCM-D)

The film formation was studied under an applied current using a QE 401 instrument with a QEM 401 electrochemical cell with platinum coated crystal QSX 314 both purchased from Q-Sense, Sweden. This instrument allows us to precisely quantify any mass adsorbed on the surface with a detection limit of theoretically 0.5 ng/cm$^2$. The crystals were cleaned in 2% sodium dodecyl sulfate (SDS) for 30 min, rinsed with H2O and blow dried with N2. The surface was cleaned in a final step in UV/O3 treatment (UVO Cleaner, Jelight Inc., USA) for 30 min. After mounting the crystal in the electrochemical cell (EC) of the QCM-D, artificial urine was pumped through the heated EC cell (37° C.) and the selected current was applied by an Autolab potentiostat (Eco Chemie, Netherlands).

For flat, uniform and rigid films adsorbed on a QCM crystal the measured change in resonance frequency is directly proportional to the adsorbed mass given by the Sauerbrey relationship. In the present case, some deviation from the Sauerbrey relationship was measured, due to the visco-elastic nature of the adsorbed film and its water content. By assuming a Voight model, using the 3th, 5th, 7th, 9th overtones according to Voinova et. al and the software package Q-Tools (Q-Sense, Sweden), it was possible to calculate the "wet" mass uptake during the current applications.

d. Atomic Force Microscopy AFM

The formed layers from the QCM experiment were investigated with atomic force microscopy (NanoWizard Bio-AFM, JPK Instruments, Germany) and Mikromasch CSC38/noAl cantilevers (contact mode, set point=0.2V). All surfaces were analyzed in dry state. The surface roughness was measured on 5 different areas with the dimension $2 \times 2$ μm, the RRIVIS value was calculated and given with standard deviation in the corresponding AFM scan images. After the AFM measurement the formed films were immersed subsequently in 1 M HCl and 1 M NaOH to test the dissolution behavior.

e. Bacterial Adherence and Survival

The flow chamber was custom-built, made of PMMA and designed for hosting the chip substrate. A peristaltic pump (IPC, ISMATEC, Switzerland) was used to maintain a constant flow rate of 200 μl/min. The flow chamber was placed in an incubator at 37° C. during the experiment, while the urine reservoir was placed outside of the incubator at room temperature. Selected currents were applied by the Autolab potentiostat (Eco Chemie, Netherlands). After the experimental time of 6 days, the cell viability and substrate were simultaneously stained with 16 μg/ml fluorescein diacetate (FDA) and 2 μg/ml propidium iodide (PI) solved in PBS. The flow cell was rinsed with the staining solution for about 5 min before rinsing with PBS and 10% formaldehyde in PBS for sample fixation. The substrate was blow dried with N2 and the electrode side was embedded in O.C.T™ Tissue Tek with a cover slide on top. The pictures were taken with a Zeiss LSM510 microscope equipped with an oil 63x/1.4 NA M27 plan-apochromat objective and EM-CCD camera from Hamamatsu.

B. Results a. Electrochemical Quartz Crystal Microbalance with Dissipation Monitoring (EC-QCM-D)

Figure 12:
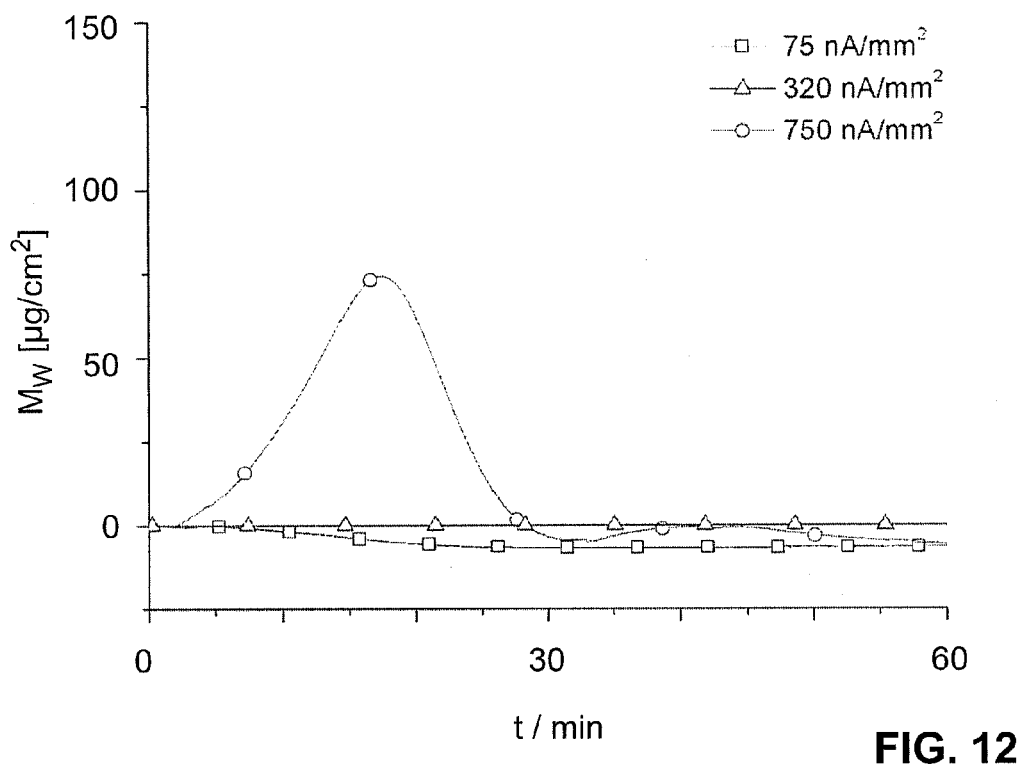
FIG. 12 is a diagram showing layer formation measured with QCM-D at different current densities applied to a platinum electrode in artificial urine; an alternating current with a period of 4 s at current densities $I=75$ nA/mm$^2$, $I=320$ nA/mm$^2$ and $I=750$ nA/mm$^2$ was applied;.
Figure 13:
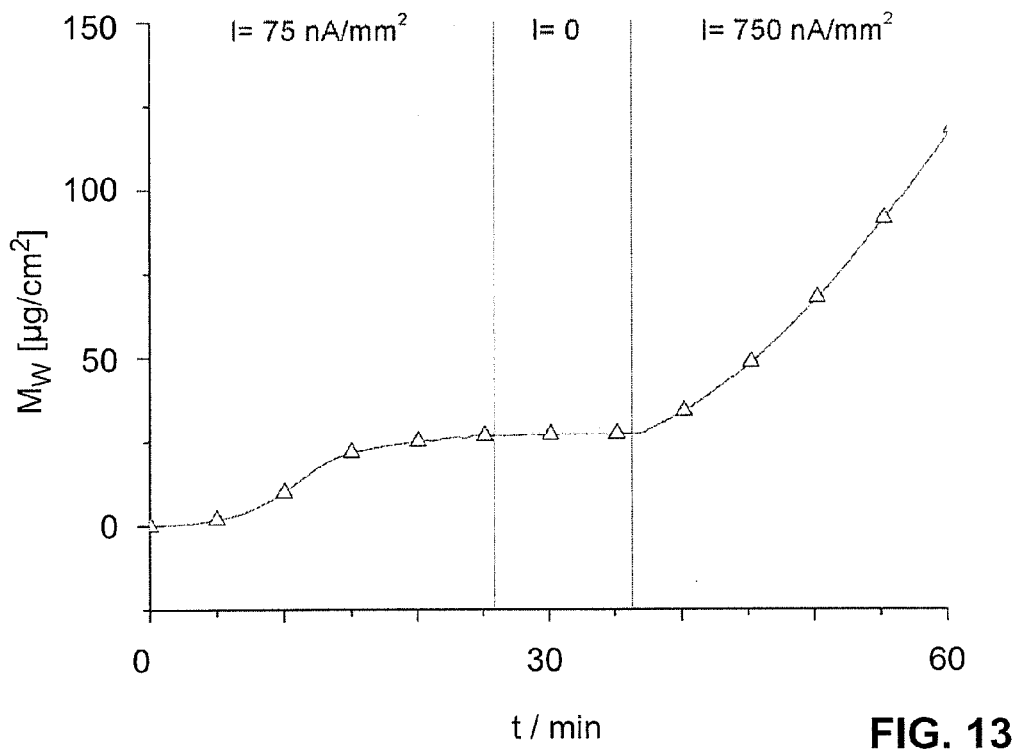
FIG. 13 is a diagram as in FIG. 11 for a constant anodic current of current densities $I=75$ nA/mm$^2$ and $I=750$ nA/mm$^2$.
Figure 14:
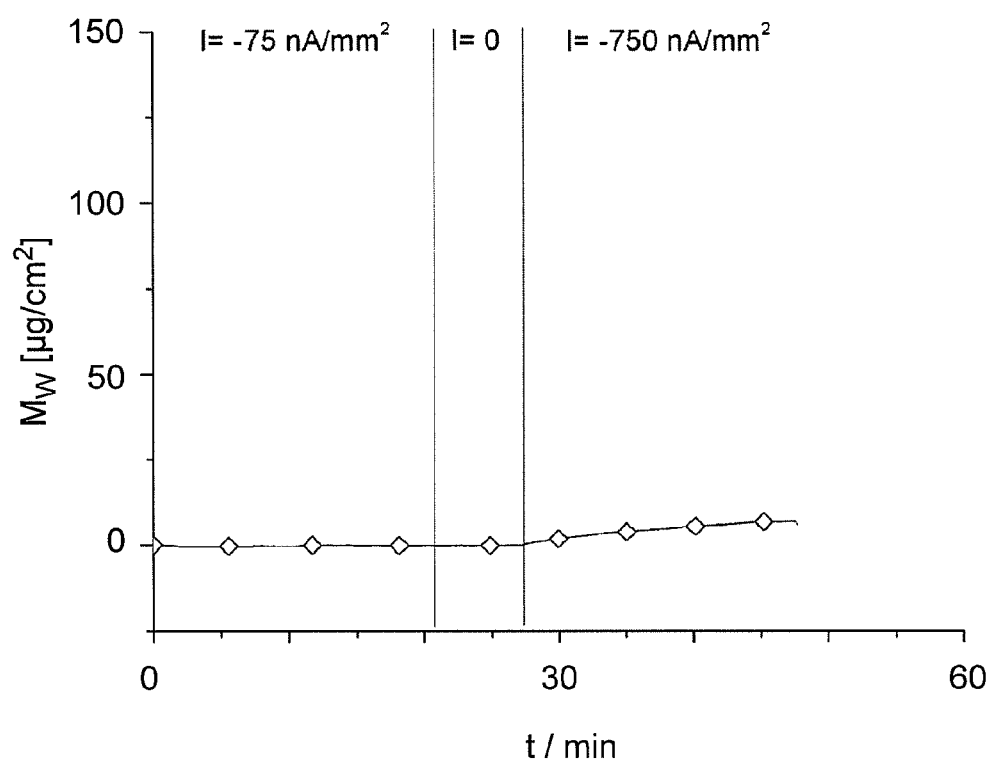
FIG. 14 is a diagram as in FIG. 11 for a constant cathodic current of current densities $I=-75$ nA/mm$^2$ and $I=-750$ nA/mm$^2$.

Different current densities were applied on the platinum coated QCM crystals and the amount of deposited material from artificial urine was monitored by the shift in the resonance frequency. Using the approximate values for the density (1000 kg/m$^3$) and the viscosity (0.001 kg/m s) of artificial urine, a fitting procedure based on the Voight model was applied and the wet mass increment of the adsorption process (0.1368 μg/Hz/cm$^2$) was determined. Using this value the adsorbed wet mass of the formed layer was calculated from the observed changes in the resonance frequencies. The same fitting procedure was used to estimate the layer formation for both, anodic and cathodic currents. An alternating current (period 4 s) density of I=75 nA/mm$^2$ was applied for 1 hour and observed a slightly decreasing baseline (to Δmaxwet mass=−6 μg/cm$^2$), see FIG. 12. At a current density of I=320 nA/ mm$^2$ (Δmaxwet mass=<0.1 μg/cm$^2$), no significant adsorption was observed. However, if a current density of I=750 nA/mm$^2$ was applied the formation of a transient film with a peak Δmaxwet mass=74 μg/cm$^2$ was observed after 18 min. Then, the film desorbed with the same rate constant as observed during formation. Applying a constant anodic current of I=75 nA/mm$^2$ showed a continuous film formation reaching a plateau at Δmaxwet mass=27 μg/cm$^2$, see FIG. 13. Switching off the current (I=0) did not change the layer thickness. Increasing the current density to I=750 nA/mm$^2$ resulted in a continuous film formation with no plateau within the course of the experiment. Applying a cathodic current density of I=−75 nA/mm$^2$ showed no film formation, whereas a ten times higher current density displayed a slight film formation in the range of 6 μg/cm$^2$, see FIG. 14.

b. Atomic Force Microscopy AFM

The platinum coated QCM crystals were gently rinsed with H$_2$O and blow dried with N$_2$ after the measurements. Macroscopically, the surfaces from the alternating and cathodic current experiment were clean, whereas the surface from the anodic current was covered with a bluish, oil-like film. Atomic force microscopy revealed the lack of deposited residues on the surface with applied alternating current densities I=320 nA/mm$^2$ and I=750 nA/mm$^2$, respectively. The surface roughness after current became even lower than that of the new untreated, platinum coated crystals. In contrast, the platinum surface after anodic current treatment clearly showed the presence of a film that started to delaminate from the surface and wile scanning, a small fragment of the film was removed, indicating weak film adhesion. The surface exposed after the film removal had a surface roughness of RRIVIS=1.9 nm. Due to the small delaminated area, only one $2 \times 2$ μm region could be measured inside the hole. Therefore, no standard deviation is given. The roughness of the surrounding was also RRMS=1.9 nm±0.5. The film thickness was around 50 nm in dry state. After cathodic treatment, the surface showed an increase in surface roughness to RRMS=2.8 nm±1.4 nm.

c. Dissolution Behavior

After the AFM measurement, the QCM crystals were immersed in an acidic and a basic solution to test their dissolution behavior. Surprisingly, a very thin film seemed to tear off from the surface of the QCM crystal treated with alternating current I=750 nA/mm$^2$ when immersed in acidic solution, while I=320 nA/mm2 did not show any delamination of a layer. The anodic bluish, oil-like film remained present in acidic solutions, while it was immediately dissolved in basic solutions. The cathodic QCM crystal showed no change in either of the solutions.

d. Bacterial Adherence and Survival

The experiment with *Proteus mirabilis* containing artificial urine was performed in the custom-built flow cell (FIGS. 9-11) sealed onto a glass substrate with 6 equal platinum electrodes. Different currents (alternating current of I=320 nA/mm$^2$, anodic currents of I=75 nA/mm$^2$ and I=750 nA/mm$^2$) were applied under continuous urine flow. After 6 days the substrate surface was stained for viable and dead cells. *Proteus mirabilis* adhered to the control electrode with no current applied. Most of the cells were found alive (green, FDA positive) and only a small fraction was dead (red, PI positive). On the electrode with alternating current of I=320 nA/mm$^2$ only few dead bacteria and some impurities were observed. On the electrode with a small anodic current of I=75 nA/mm$^2$ also only a few bacteria but a stronger green background signal was observed. At higher current density (i.e. I=750 nA/mm$^2$) a thick film started to delaminate from the electrode. The presence of spots in the image indicates that some bacteria might be incorporated in the film but it was not possible to evaluate their vital status due to the strong fluorescence of the film. The platinum electrodes were not compromised by the applied currents after 6 days and no corrosion artifacts were observed in transmission light microscopy (images not shown).

e. Discussion

Decades after the introduction of the first catheters to urology long term catheters remain to be a significant clinical problem. Biofilm formation, infection and encrustation of catheters made from synthetic materials require the use of antibiotics and often stent replacements. Therefore, the present invention suggests a novel approach, applying micro currents to electrodes to minimize biofilm formation and bacterial adherence.

First a standardized in vitro model using a custom-designed chip with 6 platinum electrodes and flowing artificial urine was developed. Among the different non-corrosive materials that could be used as electrode surface, stainless steel, gold, silver and platinum are most common. For this feasibility study it was decided to employ platinum electrodes because of their inert chemical characteristics. In this model the electrical power settings were set so low that no cytotoxic effect is expected on the mucosa of the ureter or urethra and the electrical energy applied is too low to be sensed by patients. The current density, rather than the potential, was kept constant to achieve a constant electrochemical product turnover. *Proteus mirabilis* was used because it is the most common bacteria to colonize catheter surfaces, to form extensive biofilms leading to encrustation. Furthermore, *Proteus mirabilis* produces urease, which significantly increases the local pH levels by metabolizing urea to ammonia, inducing a precipitation of calcium- and magnesium-phosphate. In principle, this strategy should be applicable to other bacteria causing urinary tract infections including *Pseudomonas aeruginosa, Klebsiella pneumoniae* and *Serratia*.

Applying alternating current to platinum surfaces showed different reactions on the adsorption of material depending on the current densities; at low and moderate current densities no significant mass changes on the platinum electrodes was observed. Applying a high current density, an initial buildup of the film with reduction of the film thereafter was recorded, without a change in current settings. This effect might be due to weak interaction of the film with the surface might lead to partial delamination which is then averaged by the QCM and could be not observed in the AFM analysis due to the limited scanning area (100×100 μm).

The AFM analysis of the platinum QCM crystals showed a slight increase of the surface roughness on the formed film and within the delaminated area, indicating some partial residues on the bottom surface. But the highest surface roughness was measured after applying cathodic currents, which electrochemically induced high pH and might have caused precipitation of a layer of calcium- and magnesium phosphate as indicated by the mass uptake in the QCM data at the higher current density.

The dissolution behavior of the formed layer was tested by dipping in acidic or base solution. Delamination of a barely visible film was seen when soaked in acidic solution only. The interaction force must be weaker in the presence of protons, indicating that films must have been formed at basic conditions. This can be explained by the different standard reduction potentials necessary for the electrolysis of water at the anode (1.23 V vs. NHE) and cathode (−0.83 V vs. NHE) and the symmetric current pulse applied. More hydroxide was formed at lower potentials than protons. As expected, the layer formed at anodic current was removed in basic solution.

These findings support the idea of using electric currents to prevent bacterial adhesion to urinary catheters and stents either by the electrochemical products due to Faradaic reactions and/or by altering the surface characteristics of the conditioning film. This technology could potentially be useful for all inserted urologic devices including, Foley catheters, Double-J stents, prostatic stents and nephrostomy catheters. In order to apply a micro-current to the stents the surface will have to be rendered conductive. This can be done by application of a conductive layer, e.g. silver or platinum. Further, for internal application, a micro-battery or an inductive device will be needed for energy delivery.

The present results on bacterial adherence and growth showed significantly decreased bacterial adhesion after 6 days in the case of applying alternating current (I=320 nA/mm$^2$) and the expected layer formation at anodic currents, which started to delaminate at the highest current density. The film formation under applied electric currents is different compared to conditioning films formed under normal conditions. As indicated by the present results, the likelihood of bacterial adhesion to such an altered surface might be lower than under normal conditions and the electrochemical products $H^+$, $OH^{-60}$ generated on the electrode surface create unfavorable chemical gradient for bacterial colonization. Moreover, HClO is a strong oxidizer with bactericide properties in the vicinity of the electrode, where antibiotics usually cannot be applied in high enough concentrations and $H^+$ is changing the urine's pH to low values preventing calcium- and magnesium phosphate precipitation. No microscopic crystals on the electrodes were observed throughout the experimental time.

In conclusion, it was shown that micro-current applied to a conducting surface is effective in reducing bacterial growth in two ways. First, it can reduce the formation of the conditioning layer making bacterial adherence more difficult and secondly, by changing the microenvironment preventing bacterial adherence and growth.

The invention claimed is:

1. A medical device comprising:
   a functional unit for permanent or temporary placement in the urogenital tract of a human or animal body, the functional unit having at least one electrically conducting portion; and
   a power source operable to supply a voltage and/or current to the electrically conducting portion after placement of the functional unit in the urogenital tract in a manner effective to reduce the growth of bacteria and/or encrustation on the functional unit wherein the power source is operable to supply said current in a manner to generate a surface current density between 10 nA/mm$^2$ and 10,000 nA/mm2 between a surface of said functional unit and environmental body material.

2. The device of claim 1, wherein the power source is operable to supply said current as an alternating current with a frequency below 1 kHz.

3. The device of claim 1, wherein the power source is operable to supply the current with a predetermined single polarity, the functional unit acting as an anode for said current.

4. The device of claim 1, wherein the functional unit is a Foley catheter, a ureteric stent, a prostatic stent or a nephrostomy catheter.

5. The device of claim 1, wherein the power source comprises a battery to be placed inside the human or animal body.

6. The device of claim 1, wherein the power source comprises:
   an energy transmitter to be placed outside the human or animal body, the energy transmitter being operable to transmit energy from outside the body to a location inside the body in a contact-less fashion;
   an energy receiver to be placed inside the human or animal body, the energy receiver being operable to receive energy from the energy transmitter in a contact-less fashion when implanted in the body.

7. The device of claim 6, wherein the energy transmitter is operable to generate an electromagnetic field, and wherein the energy receiver is operable to receive the electromagnetic field generated by the energy transmitter and to convert said electromagnetic field into an electrical current.

8. The device of claim 1, comprising:
   a first inductor operable to generate a substantial magnetic field acting on the functional unit; and
   a voltage generator operable to supply said first inductor with a time-dependent first voltage,
   wherein the functional unit represents a second inductor which, after placement of the functional unit in the urogenital tract and after placement of the first inductor in the vicinity of the functional unit, is inductively coupled with said first inductor to induce a second voltage in said functional unit via a time-dependent magnetic field generated by a time-dependent current in said first inductor caused by said first voltage.

9. The device of claim 8, wherein the second inductor has a first and a second electrode connected with the second inductor, and wherein, after placement of the functional unit in the urogenital tract, the first and second electrode are electrically connected with environmental body material in a manner that the second voltage causes a current to flow through the body material.

10. The device of claim 8, wherein the second inductor has a first and a second terminal, wherein the first and second terminal are electrically connected to form a closed circuit with the second inductor, and wherein the voltage generator is operable to supply the time-dependent first voltage in a manner to induce a closed-loop current in the closed circuit.

11. The device of claim 1, wherein the power source comprises:
   a first electrode placed in the vicinity of said functional unit to form a capacitance with the functional unit;
   a second electrode placed in environmental body tissue;
   and a voltage generator operable to supply said first electrode and said second electrode with a time-dependent first voltage so as to cause a capacitive current between the first electrode and the functional unit and an ionic current between the functional unit and the second electrode.

12. The device of claim 1, where the functional unit comprises a drug releasable from the functional unit, and wherein the device is operable to control release of said drug by means of said voltage and/or current.

13. The device of claim 1, wherein the functional unit is at least partially resorbable, and wherein the device is operable to control a rate of resorption by means of said voltage and/or current.

14. The device of claim 1, wherein the functional unit comprises:
   an electrically conductive polymer; or
   a polymer matrix with an electrically conductive filler material in the form of particles, fibers, or nanotubes.

15. The device of claim 1, wherein the functional unit has at least two electrodes connectable to environmental body material, the electrodes being connected by an inductor operable to receive a time-dependent magnetic field so as to induce a voltage between said electrodes.

16. The device of claim 15, wherein the functional unit is a stent defining a stent axis, and wherein the inductor defines a current path that is substantially helicoidal around said stent axis.

17. A method of reducing bacterial growth and/or encrustation on a functional unit inserted into the urogenital tract of a human or animal body so as to be in contact with urine, the method comprising:
   applying a voltage and/or current to the functional unit after insertion into the urogenital tract in a manner effective to reduce bacterial growth and/or encrustation, wherein a current having a surface current density between 10 $nA/mm^2$ and 10,000 $nA/mm^2$ is generated between a surface of said functional unit and environmental body material.

18. The method of claim 17, wherein the current is applied as an AC current with a frequency below 1 kHz.

19. The method of claim 17, wherein the current is applied only in a predetermined direction, the functional unit acting as a cathode for said current.

* * * * *